(12) United States Patent
Best

(10) Patent No.: US 10,383,365 B2
(45) Date of Patent: Aug. 20, 2019

(54) CRAVING SUPPRESSION METHOD AND NON-ELECTRIC NICOTINE DELIVERY SYSTEMS AND METHOD OF USE THEREOF

(71) Applicant: Daniel Best, Columbus, GA (US)

(72) Inventor: Daniel Best, Columbus, GA (US)

( * ) Notice: Subject to any disclaimer, the term of this patent is extended or adjusted under 35 U.S.C. 154(b) by 244 days.

(21) Appl. No.: 15/426,299

(22) Filed: Feb. 7, 2017

(65) Prior Publication Data
US 2018/0220704 A1 Aug. 9, 2018

(51) Int. Cl.
*A24F 47/00* (2006.01)
*A61M 11/00* (2006.01)
*A61M 15/00* (2006.01)

(52) U.S. Cl.
CPC .......... *A24F 47/00* (2013.01); *A61M 11/006* (2014.02); *A61M 15/0001* (2014.02); *A61M 15/0003* (2014.02); *A61M 15/0025* (2014.02); *A61M 15/0065* (2013.01); *A61M 15/0091* (2013.01)

(58) Field of Classification Search
CPC ................................ A24F 47/00; A61M 11/06
USPC ............. 128/200.11, 202.21, 203.11–203.22; 131/275
See application file for complete search history.

(56) References Cited

U.S. PATENT DOCUMENTS

| | | | | |
|---|---|---|---|---|
| 6,044,841 A * | 4/2000 | Verdun | ................... | A61M 11/06 128/200.14 |
| 6,125,844 A * | 10/2000 | Samiotes | .......... | A61M 15/0065 128/200.12 |
| 8,813,759 B1 | 8/2014 | Horian | | |
| 9,380,810 B2 | 7/2016 | Rose et al. | | |
| 9,757,528 B2 * | 9/2017 | Rubin | ..................... | A61M 11/02 |
| 2004/0065324 A1 * | 4/2004 | Pivinski | ............ | A61M 15/0023 128/200.23 |
| 2008/0241255 A1 * | 10/2008 | Rose | .................. | A61K 31/4439 424/489 |
| 2010/0154793 A1 * | 6/2010 | Kobayashi | ........... | A61M 11/007 128/203.14 |
| 2011/0036346 A1 * | 2/2011 | Cohen | ............... | A61M 15/0065 128/200.14 |
| 2014/0000638 A1 * | 1/2014 | Sebastian | ............... | A24F 47/008 131/328 |
| 2014/0378790 A1 * | 12/2014 | Cohen | .................... | A61B 5/486 600/309 |
| 2015/0209530 A1 * | 7/2015 | White | .................. | A61M 11/042 424/729 |
| 2015/0216237 A1 * | 8/2015 | Wensley | ............... | A24F 47/008 131/273 |
| 2016/0242467 A1 * | 8/2016 | Vaughn | ................. | A24F 47/008 |
| 2017/0238605 A1 * | 8/2017 | Matsumoto | ............. | A24F 47/00 |

OTHER PUBLICATIONS http//www.nicorette.ca/products/quickmist NICORETTE® QUICKMIST® Fast Craving Relief Product Information, 5 pages, Nov. 28, 2016.

* cited by examiner

Primary Examiner — Nina Bhat
(74) Attorney, Agent, or Firm — Troutman Sanders LLP; Brennan Carmody

(57) ABSTRACT

A nicotine delivery system including: a first reservoir configured to contain a nicotine solution; a second reservoir configured to contain another edible liquid; and a cap attached to the first reservoir and the second reservoir, the cap including: a nozzle; and a spray mechanism that, when activated, controls an amount of the nicotine solution from the first reservoir and an amount of the edible liquid from the second reservoir to be emitted through the nozzle as a spray.

17 Claims, 10 Drawing Sheets

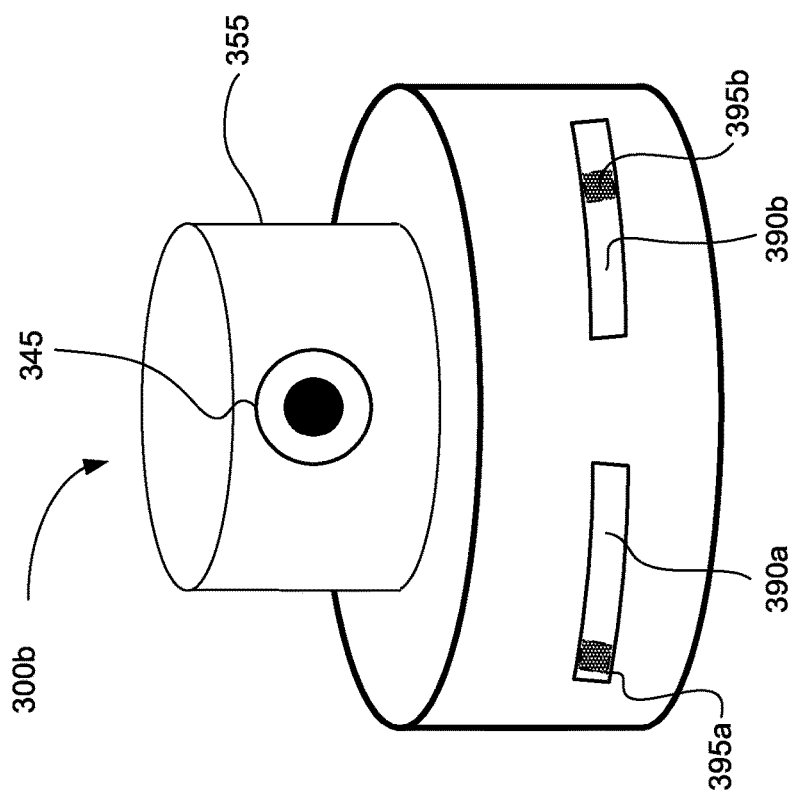
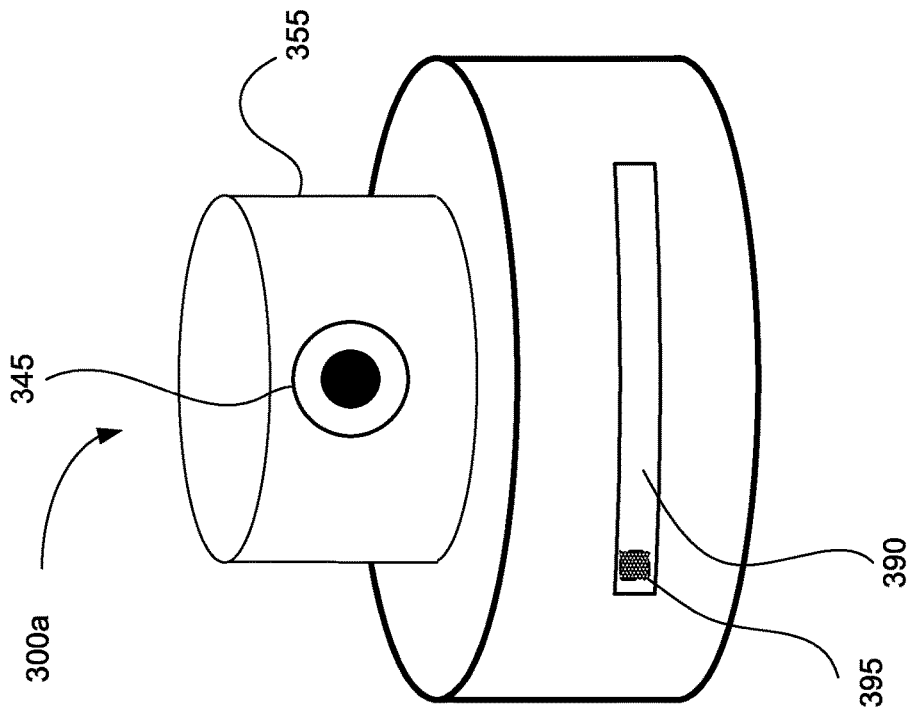

CRAVING SUPPRESSION METHOD AND NON-ELECTRIC NICOTINE DELIVERY SYSTEMS AND METHOD OF USE THEREOF

FIELD

The present disclosure relates to alternatives to smoking tobacco, and more particularly to nicotine craving suppression and non-electric nicotine delivery systems and methods of use thereof.

BACKGROUND

Smoking in considered a contributing factor to a number of diseases including respiratory diseases such as emphysema, chronic bronchitis, lung infections and lung cancer. Regular smokers often become addicted to, or dependent upon, the pharmacological effects of nicotine in tobacco smoke.

Various nicotine replacement therapies have been developed using nicotine substitutes. Nicotine substitutes generally contain nicotine in a solid form or in a solution. For example, nicotine replacement therapy has included the use of nicotine gum. However, nicotine gum provides lower nicotine levels than smoking cigarettes, and may cause gastrointestinal side effects, hiccups, ulcers, and sore throats. In addition, the amount of absorbed nicotine varies by user, based on, for example, chewing speed and saliva production. Nicotine patches have also been developed to curb cigarette cravings. However, nicotine patches may provide slow absorption and may cause skin irritation.

In the related art, a nicotine solution has been used in a spray. However, such related art sprays do not provide for variable dosage control, differing mediums for nicotine provision, or smoking like sensations. Therefore, improved nicotine suppression methods and nicotine delivery systems are needed.

SUMMARY

Disclosed and claimed herein are methods, devices and systems for delivering nicotine. One embodiment is directed to a nicotine delivery system including: a first reservoir configured to contain a nicotine solution; a second reservoir configured to contain another edible liquid; and a cap attached to the first reservoir and the second reservoir, the cap including: a nozzle; and a spray mechanism that, when activated, controls an amount of the nicotine solution from the first reservoir and an amount of the edible liquid from the second reservoir to be emitted through the nozzle as a spray.

The nicotine delivery system may further include a dosage control mechanism configured to control the amount of nicotine solution emitted by the spray mechanism.

The nicotine delivery system may further include a dosage control mechanism configured to control the amount of nicotine solution and the amount of the edible liquid emitted by the spray mechanism The nicotine delivery system may further include: a first dosage control mechanism configured to control the amount of nicotine solution emitted by the spray mechanism; and a second dosage control mechanism configured to control the amount of the edible liquid emitted by the spray mechanism.

The nicotine delivery system may further include a flavoring substance. In response to activation of the spray mechanism, a flavor from the flavoring substance may be imparted to the nicotine solution spray.

The nicotine delivery system may further include an infusion chamber. The flavoring substance may be disposed within the infusion chamber.

The infusion chamber may be disposed in a path of the nicotine solution as the nicotine solution is moved from the first reservoir to the nozzle.

The infusion chamber may be disposed outside a path of the nicotine solution as the nicotine solution is moved from the first reservoir to the nozzle.

The first reservoir may be non-removably attached to the cap.

The second reservoir may be detachable from the cap.

According to some embodiments, there may be provided a nicotine delivery system including: a reservoir for containing a nicotine solution; and a cap attached to the reservoir, the cap including: a nozzle; a spray mechanism that, when activated, controls an amount of the nicotine solution from the reservoir to be emitted through the nozzle as a spray; and a dosage control mechanism configured to control an amount of nicotine solution emitted by the spray mechanism.

According to some embodiments, there may be provided a nicotine delivery system including: a reservoir for containing a nicotine solution; and a cap attached to the reservoir, the cap including: a nozzle; a spray mechanism that, when activated, controls an amount of the nicotine solution from the reservoir to be emitted through the nozzle; and a flavoring substance, wherein, in response to activation of the spray mechanism, a flavor from the flavoring substance is imparted to the nicotine solution spray.

The nicotine delivery system may further include an infusion chamber. The flavoring substance may be disposed within the infusion chamber.

The infusion chamber may be disposed in a path of the nicotine solution as the nicotine solution is moved from the first reservoir to the nozzle.

The infusion chamber may be disposed outside a path of the nicotine solution as the nicotine solution is moved from the first reservoir to the nozzle.

The nicotine delivery system may further include a dosage control mechanism configured to control an amount of nicotine solution emitted by the spray mechanism.

According to some embodiments, there may be provided a nicotine delivery system including: a body; a first filter disposed within the body, the first filter being infused with nicotine; a second filter disposed within the body, the second filter being infused with flavoring; a mouthpiece disposed on one end of the body; and an air space disposed on the body such that breathing in through the mouthpiece causes air to flow through the first filter and the second filter to the mouthpiece.

The nicotine delivery system may further include an infusion chamber having stored therein menthol.

The infusion chamber may be disposed in a flow path of air between the first filter and the second filter and the mouthpiece.

The body may include a removable base, and the first filter and the second filter may be readily replaced after removing the base.

According to some embodiments, there may be provided a nicotine craving suppression method including: placing a craving suppression device to the lips of a user, the craving suppression device including a menthol source and not including substantial amounts of nicotine; and inhaling through the craving suppression device to breathe in a mixture of air and menthol.

The nicotine craving suppression method may further include repeating the inhaling until a nicotine craving is suppressed.

The nicotine craving suppression device may include a menthol filter.

A size and a shape of the nicotine craving suppression device may be substantially similar to a cigarette.

BRIEF DESCRIPTION OF THE DRAWINGS

The features, objects, and advantages of the present disclosure will become more apparent from the detailed description set forth below when taken in conjunction with the drawings in which like reference characters identify correspondingly throughout and wherein:

FIGS. 3A and 3B depict representations of spray caps according to example embodiments.

DETAILED DESCRIPTION

Figure 1:
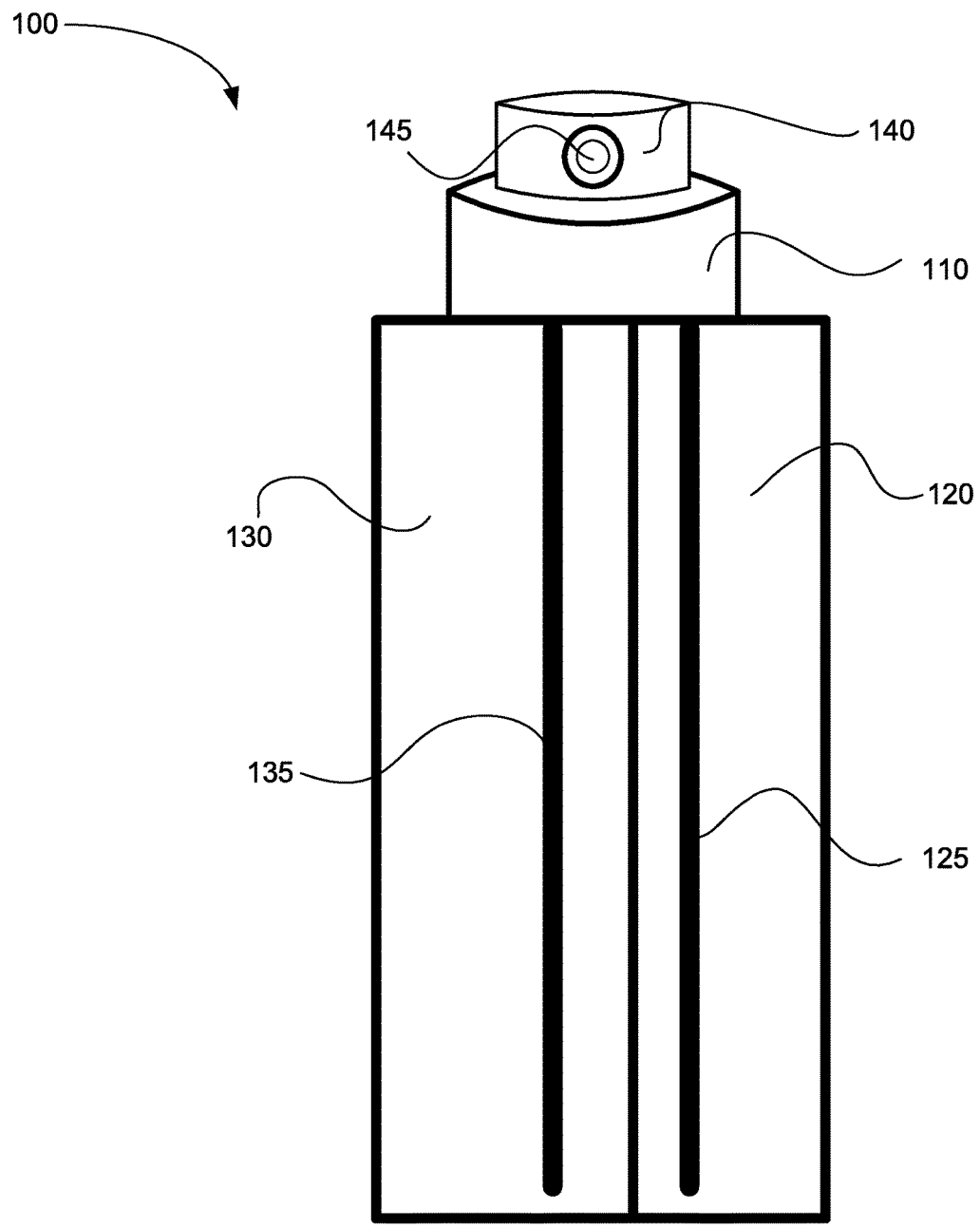
FIG. 1 depicts a representation of a nicotine delivery system according to an example embodiment.

One aspect of the disclosure relates to providing a nicotine delivery system. In some embodiments, the system includes a spraying mechanism with a first and a second reservoir. A nicotine solution is stored in the first reservoir. In the second reservoir, an additional liquid is stored. When the spraying mechanism is activated, a spray including a mix of the nicotine solution with the additional liquid is emitted from the system. In some cases, a dosage control may adjust an amount of nicotine solution emitted by the system when the spraying mechanism is activated. In some cases, the dosage control may also adjust an amount of the additional liquid emitted by the system when the spraying mechanism is activated. In some cases, a control may adjust an amount of the additional liquid emitted by the system when the spraying mechanism is activated.

In some embodiments, the system includes a spraying mechanism with a reservoir containing a nicotine solution. A flavoring substances including in a chamber mixes with air and the nicotine spray to enhance an experience of smoking. For example, the flavoring substance may include menthol.

Example implementations of the disclosed technology will now be described with reference to the accompanying figures.

Referring now to the figures, FIGS. 1-5 are used to describe nicotine delivery systems according to some embodiments. FIGS. 1-5 illustrate a nicotine spray delivery system according to some embodiments. One of ordinary skill will understand various alterations may be made to the spray delivery systems without departing from the scope of the disclosure.

FIG. 1 depicts a nicotine delivery system according to an example embodiment. According to one embodiment, nicotine delivery system 100 may be, for example, a spray bottle. According to one aspect of the disclosure, the nicotine delivery system 100 includes a cap 110 connected to two reservoirs 120 and 130. The first reservoir 120 contains a nicotine solution, while the second reservoir 130 contains another liquid. As non-limiting examples, the second reservoir may contain water, soda, or an alcoholic beverage. In some cases, the second reservoir may contain a solution of menthol. In such case, a sensation of use of the system 100 may more closely mimic a feeling of smoking tobacco. The first reservoir 120 and the second reservoir 130 may be of a same or different size, shape, and/or volume.

The cap 110 may include a spray mechanism 140. A first tube 125 extends from the spray mechanism 140 into the first reservoir 120. A second tube 135 extends from the spray mechanism 140 into the second reservoir 130. When the spray mechanism 140 is activated, a portion of the nicotine solution in the first reservoir 120 and a portion of the fluid in the second reservoir 130 is output through a nozzle 145 of the spray mechanism. In some cases, a same amount of fluid from the first reservoir 120 and the second reservoir 130 may be emitted from the nozzle 145 when the spray mechanism 140 is activated. In some cases, as a non-limiting example, the spray mechanism 140 may be activated by pushing a portion of the cap 130 downward. In some cases, the spray mechanism 140 may be breath-actuated.

In some embodiments, the first reservoir 120 and the second reservoir 130 may be joined together as a unit and separated by a dividing wall. In some embodiments, the first reservoir 120 and the second reservoir 130 may be separately detachable from the cap 110. In some embodiments, the first reservoir 120 may not be readily separable from the cap 110, e.g., adhered to or formed together with the cap, while the second reservoir 120 may be readily removable to be filled with a second fluid.

FIG. 2A depicts a spray cap according to an example embodiment. The spray cap 200*a* includes a nozzle 245, an action mechanism 255, and a spring 265. The action mechanism 255 may be of various types, for instance, a press-type mechanism. When the action mechanism 255 is activated, liquid (i.e., the nicotine solution and the second fluid) are forced from the first reservoir and the second reservoir and sprayed from the nozzle 245. When the action mechanism 255 is release, the spring 265 resets the action mechanism 255 for a next use. One of ordinary skill will recognize that the action mechanism 255 depicted in FIG. 2A is merely an example, various types of action mechanisms may be utilized within the scope of the present disclosure. In some cases, the action mechanism 255 may be a breath-actuated mechanism, as discussed in more detail below with reference to FIG. 4.

FIG. 2B depicts a spray cap according to another example embodiment. Similar to the spray cap 200*a*, the spray cap 200*b* includes a nozzle 245, an action mechanism 255, and a spring 265. The spray cap 200*b* further includes an infusion chamber 275. Inside the infusion chamber 275 is a flavoring mechanism 285, e.g., a flavoring substance. As the liquid is forced from the reservoir to the nozzle 245, a flavor of the flavoring mechanism 285 is imparted to the spray. As a non-limiting example the flavoring mechanism 285 could be menthol balls. The menthol balls may be used to impart a sensation more similar to smoking tobacco.

One of ordinary skill will recognize that the infusion chamber 275 depicted in FIG. 2B is merely exemplary, and that various modifications may be made thereto. As a non-limiting example, the infusion chamber 275 may be disposed separate from a path of the liquid from the first and second reservoirs. The action mechanism 285 may control air to pass over or through the infusion chamber 275 and mix with the spray containing the nicotine solution.

FIG. 3A depicts a spray cap according to an example embodiment. The spray cap 300a includes a nozzle 345, an action mechanism 355, and a dosage control mechanism 390. The action mechanism 355 may be of various types, for instance, a press-type mechanism. When the action mechanism 355 is activated, liquid (i.e., the nicotine solution and the second fluid) are forced from the first reservoir and the second reservoir and sprayed from the nozzle 345. The dosage control mechanism 390, i.e., the dosage control, controls an amount of fluid that is emitted from the first reservoir (i.e., the nicotine solution) in response to the action mechanism 355. In some cases, the dosage control mechanism 390 may further control an amount of fluid that is emitted from the second reservoir in response to the action mechanism 355. The dosage control mechanism 390 may be a slide-type control and may include a slider 395. However, this is a non-limiting example, and one of ordinary skill will understand that the dosage control mechanism 390 may take many forms.

FIG. 3B depicts a spray cap according to another example embodiment. Similar to the spray cap 300a, the spray cap 300b includes a nozzle 345 and an action mechanism 355. The spray cap 300b further includes a first dosage control mechanism 390a and a second dosage control mechanism 390b. The first dosage control mechanism 390a may control an amount of fluid that is emitted from the first reservoir (i.e., the nicotine solution) in response to the action mechanism 355. The second dosage control mechanism 390b may control an amount of fluid that is emitted from the second reservoir in response to the action mechanism 355. By adjusting the first and second dosage control mechanisms 390a and 390b, a ratio of nicotine solution to other fluid may be selected. In some cases, the first and second dosage control mechanisms 390a and 390b may each be slider-type mechanisms with respective first and second sliders 395a and 395b. In some cases, the first dosage control mechanism 390a may have a different form than the second dosage control mechanism 390b.

Figure 4:
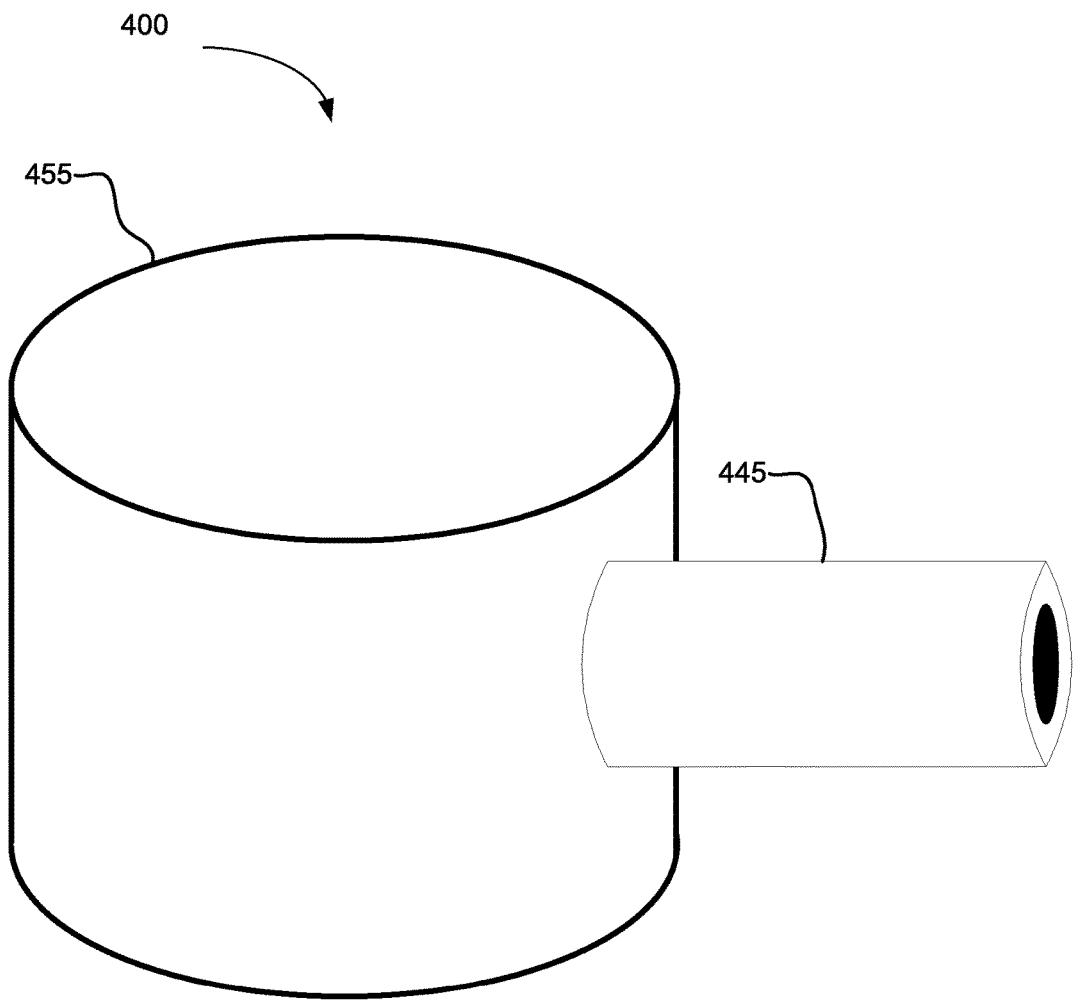
FIG. 4 depicts a representation of a spray cap according to an example embodiment.

FIG. 4 depicts a profile view of a spray cap according to another example embodiment. According to one embodiment, the spray cap 400 may include a cap hub 455 and a mouth piece 445. The hub 455 may surround a breath-actuated action mechanism. One of ordinary skill would understand how to implement a breath-actuated action mechanism, for example, one disclosed in U.S. Pat. No. 6,044,841, the disclosure of which is incorporated herein by reference in its entirety.

A user may place the mouth piece 445 into the user's mouth. As a user breathes in through the mouthpiece, the breath-actuated action mechanism is activated. Liquid (i.e., the nicotine solution and the second fluid) are forced from the first reservoir and the second reservoir and emitted, mixed with air, through the mouthpiece. In some cases, the spray cap 400 may be act as a breath-actuated nebulizer. In some embodiments, the spray cap may include one or more dosage controls that control an amount of liquid from the first reservoir and the second reservoir that is emitted in response to the breath actuation.

Figure 5:
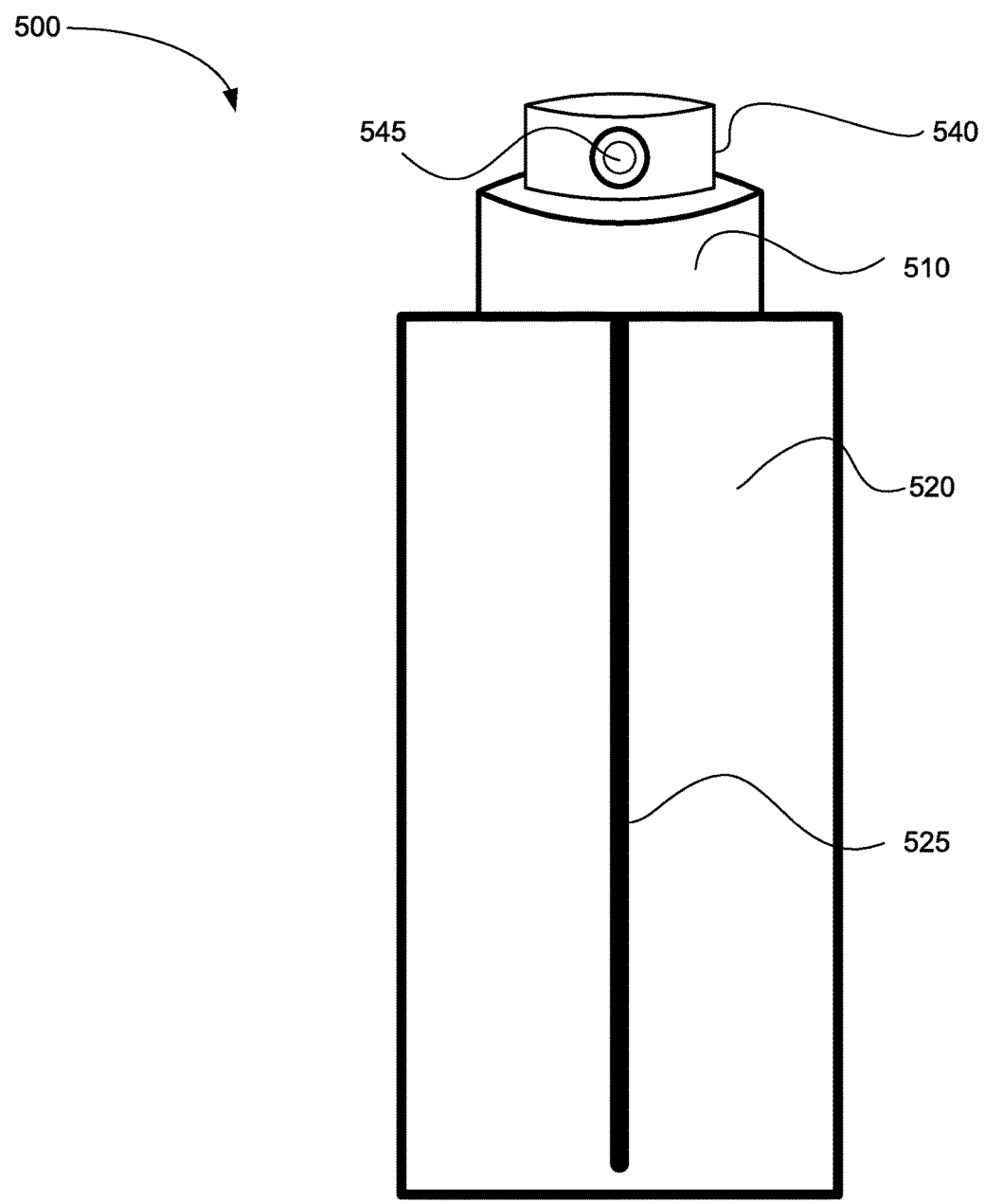
FIGS. 5-8 depict representations of nicotine delivery systems according to various example embodiments.

FIG. 5 depicts a nicotine delivery system according to an example embodiment. According to one embodiment, nicotine delivery system 500 may be, for example, a spray bottle. According to one aspect of the disclosure, the nicotine delivery system 500 includes a cap 510 and a reservoir 520. The reservoir 520 contains a nicotine solution.

Figure 2B:
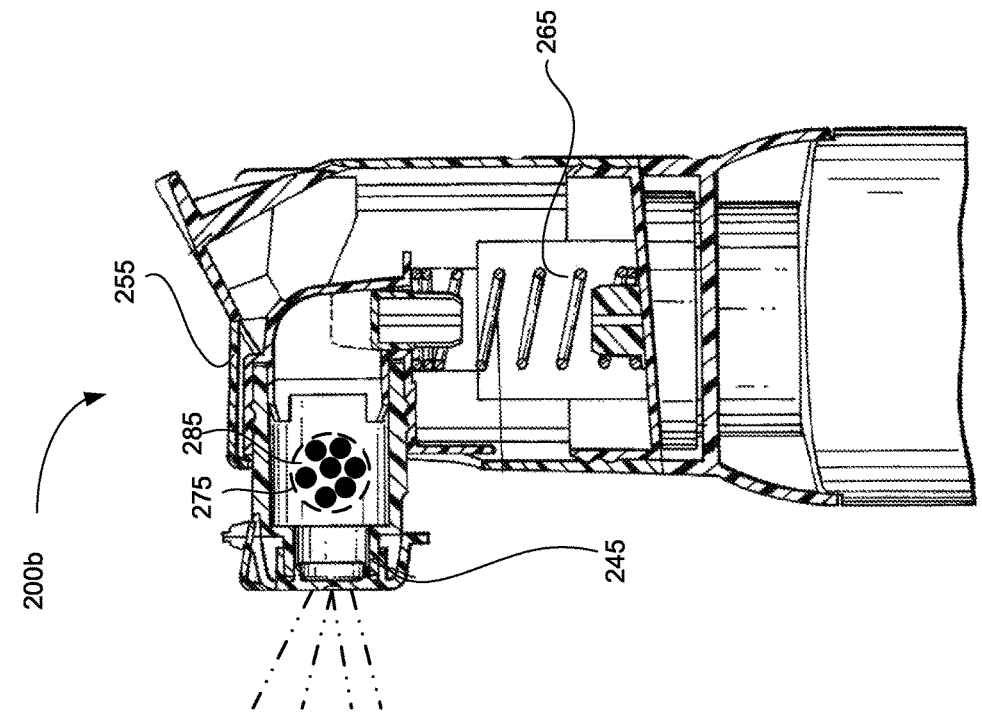
FIGS. 2A and 2B depict representations of spray caps according to example embodiments.
Figure 2A:
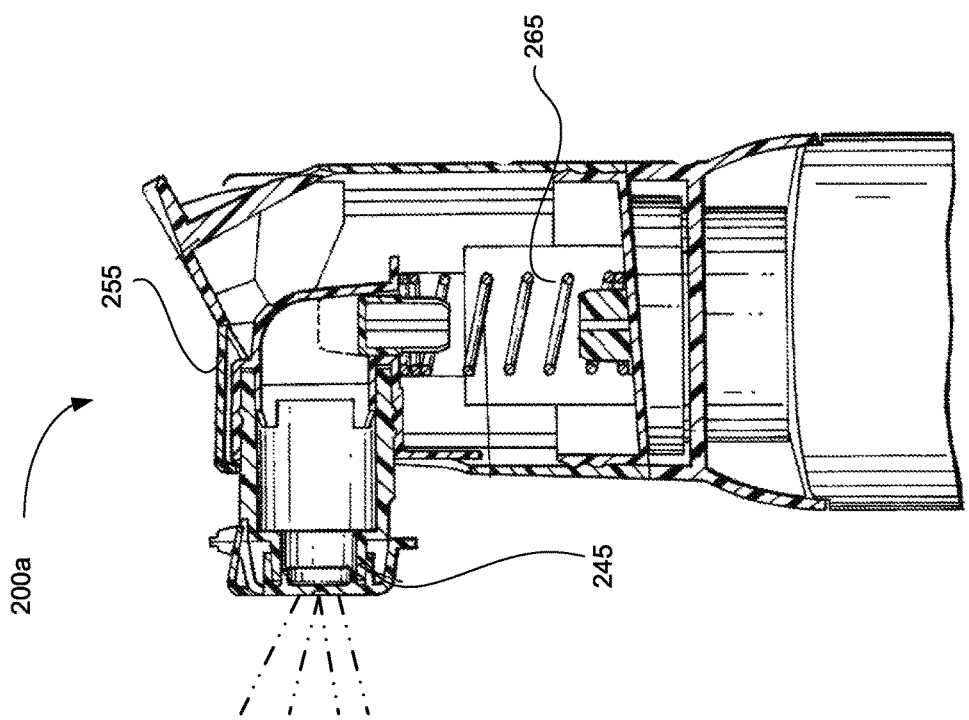

The cap 510 may include a spray mechanism 540. A tube 525 extends from the spray mechanism 540 into the reservoir 520. When the spray mechanism 540 is activated, a portion of the nicotine solution in the reservoir 520 is output through a nozzle 545 of the spray mechanism. The cap 510 may include an infusion chamber that imparts flavoring to the spray, similar to that disclosed with reference to FIG. 2B. In some cases, the cap 510 may include a dosage control mechanism that adjusts an amount of nicotine solution that is emitted from the nozzle 545 in response to activation of the spray mechanism, similar to that discloses above with reference to FIGS. 3A and 3B. In some embodiments, the cap 510 may include a breath actuated action mechanism, as discussed above with reference to FIG. 4. One of ordinary skill will understand that, in a case of a single reservoir, only the nicotine solution would be emitted from a nozzle or mouthpiece of the cap in response to the activation mechanism 540 being activated.

Figure 6:
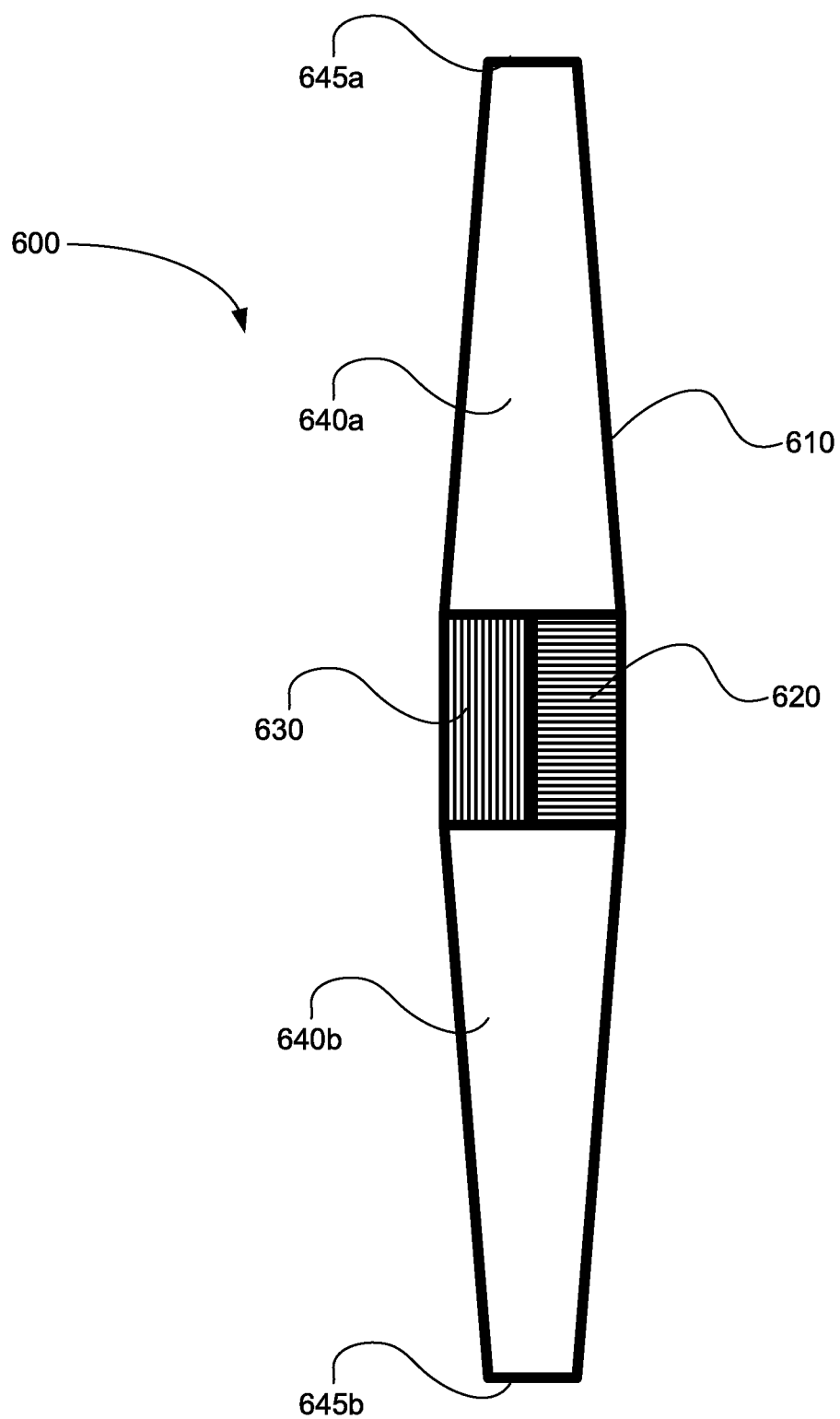
Figure 7:
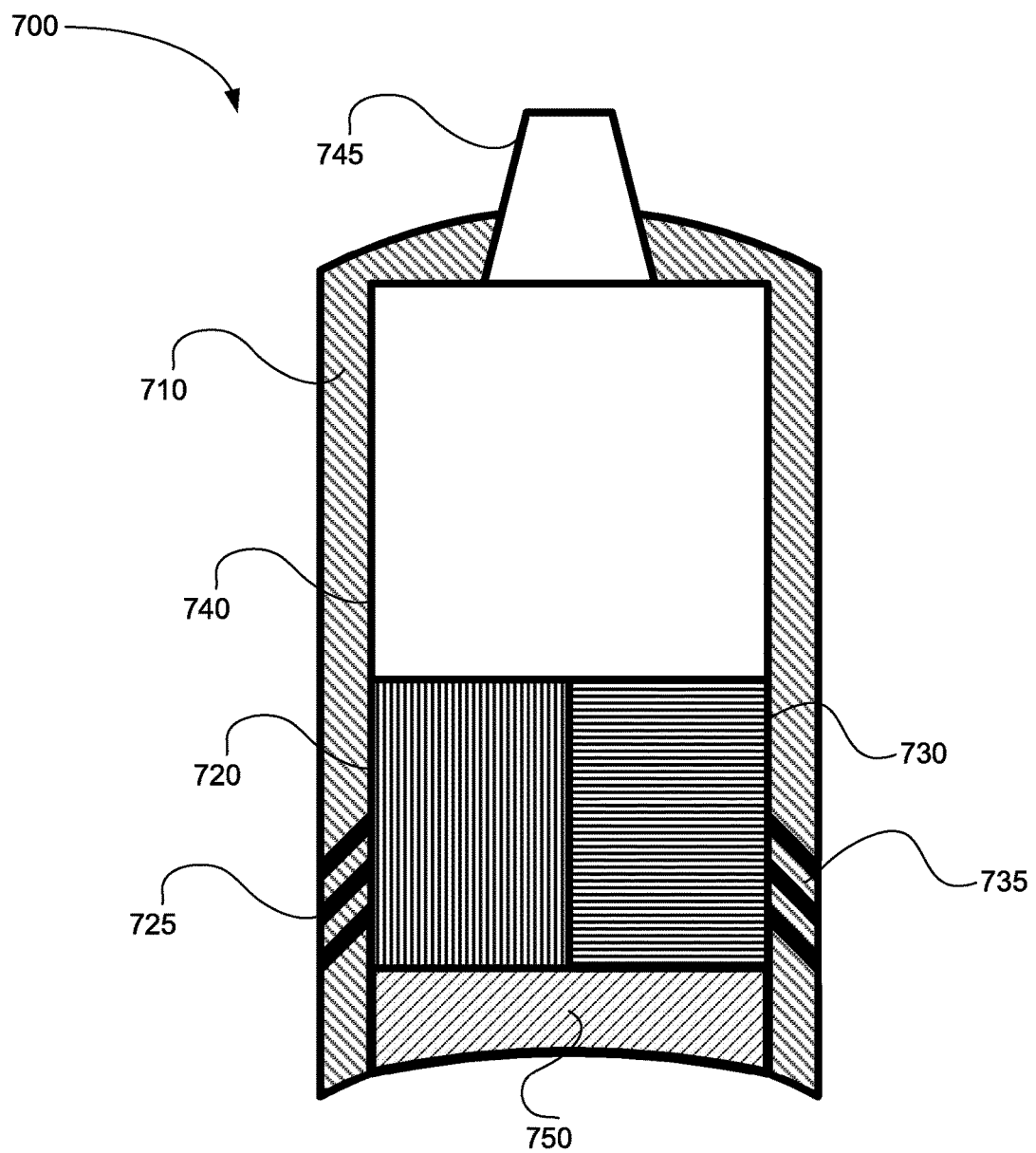

FIGS. 6-7 illustrate a nicotine inhaler delivery system according to some example embodiments. One of ordinary skill will understand various alterations may be made to the inhaler delivery systems without departing from the scope of the disclosure.

FIG. 6 depicts a nicotine delivery system according to an example embodiment. According to one embodiment, nicotine delivery system 600 may be, for example, an inhaler. According to one aspect of the disclosure, the nicotine delivery system 600 includes an outside wall 610 surrounding a first filter 620, a second filter 630, and first and second sides 640a and 640b. The first filter 620 may be infused a nicotine solution or a nicotine powder. The second filter 630 may be infused with an alternative liquid or flavoring powder. For example, the second filter 630 may be infused with soda or an alcoholic beverage. In some cases, the second filter 630 may be infused with a menthol liquid or may be a filter containing, for example, a menthol ball.

A first end 645a of the first side 640a and a second end 645b of the second side 640b may be porous to air or open. A user may breathe in through the first end 645a of the nicotine delivery system 600, and air will pass into the second end 645b, through the first filter 620 and the second filter 630, and impart some nicotine and flavoring to air breathed by the user. In some cases, the user may be able to breathe in through either the first end 645a or the second end 645b.

FIG. 7 depicts a nicotine delivery system according to another example embodiment. According to one embodiment, nicotine delivery system 700 may be, for example, an inhaler-type system. According to one aspect of the disclosure, the nicotine delivery system 700 includes a body 710 surrounding a first filter 720, a second filter 730, and a mixing chamber 740. The first filter 720 may be infused with a nicotine solution or a nicotine powder. The second filter 730 may be infused with an alternative liquid or flavoring powder. For example, the second filter 730 may be infused with soda or an alcoholic beverage. In some cases, the second filter 730 may be infused with a menthol liquid or may be a filter containing, for example, a menthol ball.

Porous areas, such as slits 725 and 735, are formed in the sides of the body 710. A user may breathe in through a mouthpiece 745 formed on one end of the body, and air will pass into the slits 725 and 735, through the first filter 720 and the second filter 730 imparting some nicotine and flavoring to air breathed by the user and mixed in the mixing chamber 740. In some cases, a base 750 of the body 710 may be removable and the first filter 720 and the second filter 730 may be replaceable. In some cases, the base 750 may be formed integrally with the first filter 720 and the second filter 730 and the unit including the base 750, the first filter 720 and the second filter 730 may be interchangeable with other units.

Figure 8:
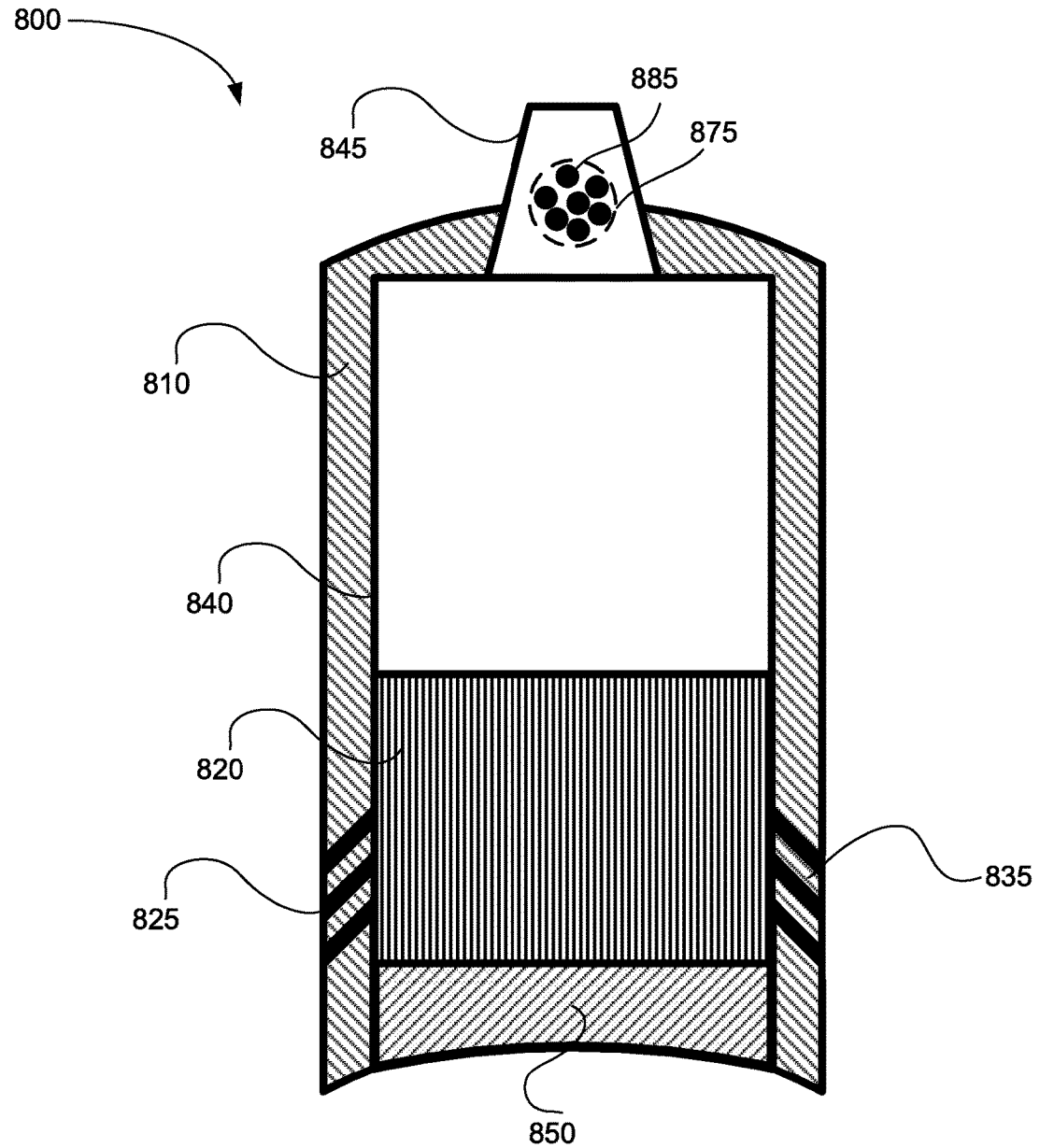

FIG. 8 depicts a nicotine delivery system according to another example embodiment. The nicotine delivery system 800 may be similar to the nicotine delivery system 700 discussed above. According to one aspect of the disclosure, the nicotine delivery system 800 includes a body 810 surrounding a filter 820 and a mixing chamber 840. The filter 820 may be infused with a nicotine solution or a nicotine powder. Porous areas, such as slits 825 and 835, are formed in the sides of the body 810, and a mouthpiece 845 is formed on one end of the body 610 adjacent to the mixing chamber 840. Inside the mouthpiece 845 is an infusion chamber 875. Inside the infusion chamber 875 is a flavoring mechanism 885, i.e., a flavoring substance. As the a user breathes in through the mouthpiece, air flows through the slits 825 and 835 through the filter 820 and is imparted with a flavor of the flavoring mechanism 885. As a non-limiting example the flavoring mechanism 885 could be menthol balls. The menthol balls may be used to impart a sensation more similar to smoking tobacco. In some cases, a base 850 of the body 810 may be removable, and the filter 820 may be readily replaceable. In some cases, the base 850 may be formed integrally with the filter 820, and the unit including the base 850 and the filter 820 may be interchangeable with other units.

Figure 9A:
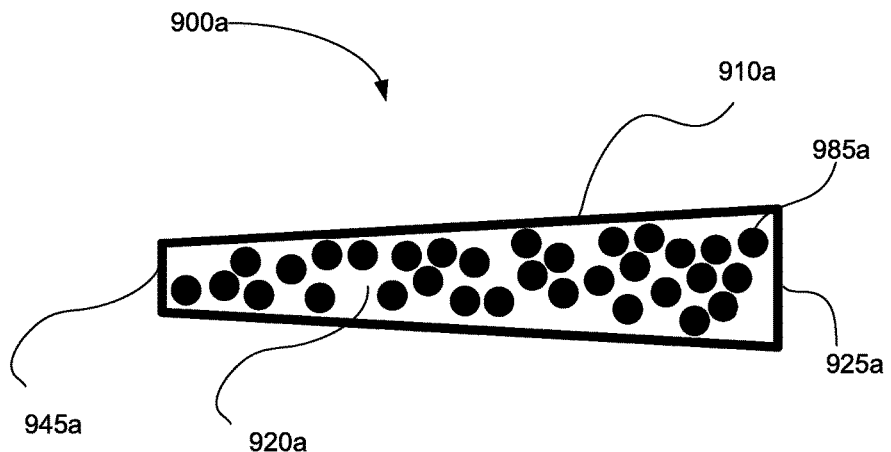
FIGS. 9A and 9B depict craving suppression systems according to example embodiments.
Figure 9B:
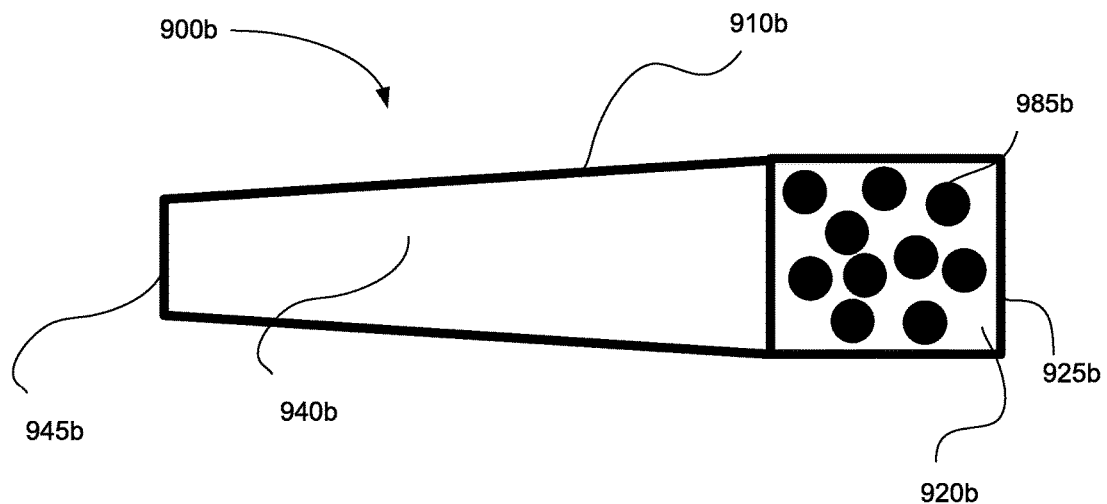

FIGS. 9A and 9B are used to describe nicotine craving suppression systems according to some embodiments. One of ordinary skill will understand various alterations may be made to the nicotine craving suppression systems without departing from the scope of the disclosure.

Referring to FIG. 9A, the nicotine craving suppression device 900a includes a body 910a having a chamber 920a. The chamber 920a contains menthol (e.g., menthol balls 985a, a filter infused with menthol powder or a menthol solution, or a reservoir including menthol). A first end 945a and a second end 925a of the chamber 920a may be substantially permeable to air. For example, the first end 945a and the second end 925a may contain slits that allow air to pass through. In a case that a user craves nicotine (e.g., desires to smoke a cigarette), the user may breathe in through the first end 945a, breathing in air infused with menthol. The menthol enthused air may provide relief from the nicotine craving. The body 910a may be substantially cylindrical or conical. In some cases, the body 910a may be sized proximate to a standard cigarette. Therefore, the tactile experience of using the craving suppression device 900a may be similar to smoking a cigarette.

Referring to FIG. 9B, the nicotine craving suppression device 900b includes a body 910b having a diffusion chamber 940b and a menthol chamber 920b. The menthol chamber 920b contains menthol (e.g., menthol balls 985b, a filter infused with menthol powder or a menthol solution, or a reservoir including menthol). A first end 945b of the diffusion chamber 940b and a second end 920b of the menthol chamber 920b may be substantially permeable to air. For example, the first end 945b and the second end 925b may contain slits that allow air to pass through. In a case that a user craves nicotine (e.g., desires to smoke a cigarette), the user may breathe in through the first end 945b, breathing in air infused with menthol. The menthol enthused air may provide relief from the nicotine craving. The body 910b may be substantially cylindrical or conical. In some cases, the body 910a may be sized proximate to a standard cigarette.

Therefore, the tactile experience of using the craving suppression device 900b may be similar to smoking a cigarette.

Figure 10:
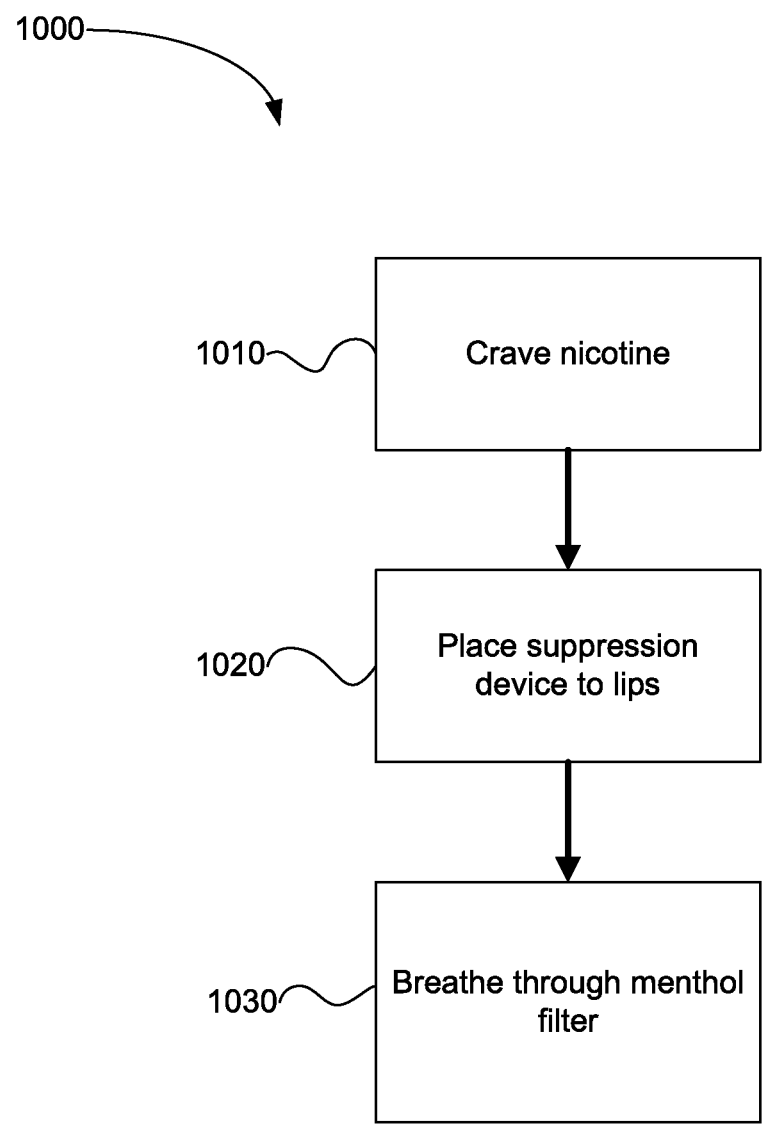
FIG. 10 is a block diagram of a craving suppression method according to an example embodiment.

FIG. 10 illustrates a method of suppressing nicotine cravings according to an example embodiment. Referring to FIG. 10, a user craves 1010 nicotine. For example, the user may desire to smoke a cigarette. The user places 1020 a nicotine craving suppression device to the user's lips. The nicotine craving suppression device may include menthol and exclude tobacco products. In some cases, the nicotine craving suppression device may not include any nicotine. As a non-limiting example, the craving suppression device may be similar to the nicotine craving suppressions systems 900a and 900b discussed above. The user breathes 1030 through the nicotine craving suppression device containing the menthol, and experiences the air infused with menthol. The menthol infused air and the tactile feeling of the using the nicotine craving suppression device suppress the user's desire for nicotine, e.g., suppress a user's desire to smoke a cigarette.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims and their equivalents. Although specific terms are employed herein, they are used in a generic and descriptive sense only and not for purposes of limitation.

In the foregoing description, numerous specific details are set forth. It is to be understood, however, that implementations of the disclosed technology may be practiced without these specific details. In other instances, well-known methods, structures and techniques have not been shown in detail in order not to obscure an understanding of this description. References to "one implementation," "an implementation," "example implementation," "various implementation," etc., indicate that the implementation(s) of the disclosed technology so described may include a particular feature, structure, or characteristic, but not every implementation necessarily includes the particular feature, structure, or characteristic. Further, repeated use of the phrase "in one implementation" does not necessarily refer to the same implementation, although it may.

Throughout the specification and the claims, the following terms should be construed to take at least the meanings explicitly associated herein, unless the context clearly dictates otherwise. The term "connected" means that one function, feature, structure, or characteristic is directly joined to or in communication with another function, feature, structure, or characteristic. The term "coupled" means that one function, feature, structure, or characteristic is directly or indirectly joined to or in communication with another function, feature, structure, or characteristic. The term "or" is intended to mean an inclusive "or." Further, the terms "a," "an," and "the" are intended to mean one or more unless specified otherwise or clear from the context to be directed to a singular form.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

This written description uses examples to disclose certain implementations of the disclosed technology, including the best mode, and also to enable any person of ordinary skill to practice certain implementations of the disclosed technology, including making and using any devices or systems and performing any incorporated methods. The patentable scope of certain implementations of the disclosed technology is defined in the claims and their equivalents, and may include other examples that occur to those of ordinary skill. Such other examples are intended to be within the scope of the claims if they have structural elements that do not differ from the literal language of the claims, or if they include equivalent structural elements with insubstantial differences from the literal language of the claims.

What is claimed is:

1. A nicotine delivery system comprising:
a first reservoir configured to contain a nicotine solution;
a second reservoir configured to contain another edible liquid;
a cap attached to the first reservoir and the second reservoir, the cap comprising:
a nozzle; and
a spray mechanism that, when activated, controls an amount of the nicotine solution from the first reservoir and an amount of the edible liquid from the second reservoir to be emitted through the nozzle as a spray;
a first adjustable dosage control mechanism configured to control the amount of nicotine solution emitted by the spray mechanism based on a current adjustment of the first adjustable dosage control mechanism; and
a second adjustable dosage control mechanism configured to control the amount of the edible liquid emitted by the spray mechanism based on a current adjustment of the second adjustable dosage control mechanism.

2. The nicotine delivery system according to claim 1, further comprising an adjustable overall dosage control mechanism configured to control both the amount of nicotine solution and the amount of the edible liquid emitted by the spray mechanism based on a current adjustment of the adjustable overall dosage control mechanism.

3. The nicotine delivery system according to claim 1, further comprising a flavoring substance,
wherein, in response to activation of the spray mechanism, a flavor from the flavoring substance is imparted to the nicotine solution spray.

4. The nicotine delivery system according to claim 3, further comprising an infusion chamber,
wherein the flavoring substance is disposed within the infusion chamber.

5. The nicotine delivery system according to claim 4, wherein the infusion chamber is disposed in a path of only the nicotine solution as the nicotine solution is moved from the first reservoir to the nozzle.

6. The nicotine delivery system according to claim 4, wherein the infusion chamber is disposed outside a path of the nicotine solution as the nicotine solution is moved from the first reservoir to the nozzle.

7. The nicotine delivery system according to claim 1, wherein the first reservoir is non-removably attached to the cap, and the second reservoir is detachable from the cap.

8. The nicotine delivery system of claim 1, wherein the first and second adjustable dosage control mechanisms are configured to be independently adjusted to modify a ratio of nicotine solution to the edible liquid emitted by the spray mechanism.

9. The nicotine delivery system of claim 1, wherein the first and second adjustable dosage control mechanisms comprise respective slider controls.

10. The nicotine delivery system of claim 1, wherein the first and second adjustable dosage control mechanisms are disposed on the cap.

11. The nicotine delivery system of claim 1, wherein
the first reservoir is non-removably attached to the cap and contains the nicotine solution; and
the second reservoir may be readily detached from and reattached to the cap such that a user may fill the second reservoir with a desired edible liquid.

12. A nicotine delivery system comprising:
a reservoir configured to contain a nicotine solution; and
a cap attached to the reservoir, the cap comprising:
a nozzle;
a spray mechanism that, when activated, controls an amount of the nicotine solution from the reservoir to be emitted through the nozzle as a spray; and
an adjustable dosage control mechanism configured to control a ratio of nicotine solution to air emitted by the spray mechanism based on a current adjustment of the adjustable dosage control mechanism.

13. A nicotine delivery system comprising:
a first reservoir containing a nicotine solution;
a second reservoir configured to contain another edible liquid;
a cap attached to the first and second reservoirs, the cap comprising:
a nozzle;
a spray mechanism that, when activated, controls an amount of the nicotine solution from the first reservoir and an amount of the edible liquid from the second reservoir to be emitted through the nozzle; and
a flavoring substance,
a first adjustable dosage control mechanism configured to control the amount of nicotine solution emitted by the spray mechanism based on a current adjustment of the first adjustable dosage control mechanism; and
a second adjustable dosage control mechanism configured to control the amount of the edible liquid emitted by the spray mechanism based on a current adjustment of the second adjustable dosage control mechanism,
wherein, in response to activation of the spray mechanism, a flavor from the flavoring substance is imparted to the nicotine solution spray.

14. The nicotine delivery system according to claim 13, further comprising an infusion chamber,
wherein the flavoring substance is disposed within the infusion chamber.

15. The nicotine delivery system according to claim 14, wherein the infusion chamber is disposed in a path of the nicotine solution as the nicotine solution is moved from the first reservoir to the nozzle.

16. The nicotine delivery system according to claim 14, wherein the infusion chamber is disposed outside a path of the nicotine solution as the nicotine solution is moved from the first reservoir to the nozzle.

17. The nicotine delivery system according to claim 13, further comprising a dosage control mechanism configured to control an amount of nicotine solution emitted by the spray mechanism.

* * * * *